US012589227B2

(12) United States Patent
Ushida et al.

(10) Patent No.: US 12,589,227 B2
(45) Date of Patent: Mar. 31, 2026

(54) GUIDE WIRES

(71) Applicant: ASAHI INTECC CO., LTD., Seto (JP)

(72) Inventors: Keisuke Ushida, Seto (JP); Naozumi Iwata, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 818 days.

(21) Appl. No.: 17/834,764

(22) Filed: Jun. 7, 2022

(65) Prior Publication Data

US 2022/0296860 A1     Sep. 22, 2022

Related U.S. Application Data

(63) Continuation of application No. PCT/JP2019/051433, filed on Dec. 27, 2019.

(51) Int. Cl.
A61M 25/09          (2006.01)

(52) U.S. Cl.
CPC ... A61M 25/09 (2013.01); *A61M 2025/09133* (2013.01); *A61M 2025/0915* (2013.01)

(58) Field of Classification Search
CPC ...... A61B 18/1492; A61B 2018/00011; A61B 2018/00351; A61B 2018/00577; A61B 2018/0091; A61B 2218/002; A61B 2562/0247; A61B 5/6852; A61M 2025/0002; A61M 2025/0681; A61M 2205/0294; A61M 2205/3317; A61M 2205/332; A61M 2205/581; A61M 2205/583; A61M 25/0133; A61M 25/0136; A61M 25/0147; A61M 25/0662;
(Continued)

(56) References Cited

U.S. PATENT DOCUMENTS

| | | |
|---|---|---|
| 2005/0096568 A1 | 5/2005 | Kato |
| 2008/0004546 A1 | 1/2008 | Kato |
| 2008/0306468 A1 | 12/2008 | Tamai et al. |

(Continued)

FOREIGN PATENT DOCUMENTS

| | | |
|---|---|---|
| JP | 3726266 B2 | 12/2005 |
| JP | 3806139 B1 | 8/2006 |

(Continued)

OTHER PUBLICATIONS

International Search Report for parent PCT Application No. PCT/JP2019/051433.

*Primary Examiner* — Alex M Valvis
*Assistant Examiner* — Anna Roberts
(74) *Attorney, Agent, or Firm* — Norton Rose Fulbright US LLP

(57)          ABSTRACT

A guide wire in which a distal end portion of the guide wire can be easily bent in a specific plane direction in shaping, is provided. A guide wire includes a core shaft having a maximum diameter in a cross section orthogonal to an axial direction of the core shaft and an orthogonal diameter in a direction orthogonal to a direction of the maximum diameter, the core shaft includes a first specific portion located on a distal end side of the core shaft and having an oblateness between 7% and 35%, where oblateness is defined as the difference between the maximum diameter and the orthogonal diameter divided by the maximum diameter. The first specific portion of the core shaft can be 5 mm or more in the axial direction.

6 Claims, 20 Drawing Sheets

(58) Field of Classification Search
CPC ................ A61M 5/1411; A61M 5/162; A61M
5/16813; F24F 1/0007
USPC ....................................................... 600/585
See application file for complete search history.

(56) References Cited

U.S. PATENT DOCUMENTS

| | | | | |
|---|---|---|---|---|
| 2009/0254000 A1* | 10/2009 | Layman | ................ | A61M 25/01 |
| | | | | 600/585 |
| 2013/0012834 A1* | 1/2013 | Tamai | ................... | A61M 25/09 |
| | | | | 600/585 |
| 2016/0008586 A1* | 1/2016 | Matsubara | ............ | A61M 25/09 |
| | | | | 604/528 |

FOREIGN PATENT DOCUMENTS

| | | | |
|---|---|---|---|
| JP | 2008-011938 | A | 7/2007 |
| JP | 2008-110266 | A | 2/2008 |
| JP | 2012-200290 | A | 3/2011 |
| JP | 2012-091070 | A | 5/2012 |
| JP | 2016-064068 | A | 4/2016 |
| JP | 5997370 | B2 | 9/2016 |
| JP | 2018-079246 | A | 5/2018 |

* cited by examiner

FIG.6

DIRECTIONALITY OF SHAPING

| SAMPLE | WIRE DIAMETER (μm) | OBLATENESS (%) | JUDGMENT |
|---|---|---|---|
| 1 | 80 | 0 | × |
| 2 | 80 | 7.5 | ○ |
| 3 | 80 | 15 | ○ |
| 4 | 80 | 23 | ○ |
| 5 | 80 | 35 | ○ |
| 6 | 80 | 38 | ○ |
| 7 | 70 | 0 | × |
| 8 | 70 | 7.5 | ○ |
| 9 | 70 | 15 | ○ |
| 10 | 70 | 23 | ○ |
| 11 | 70 | 35 | ○ |
| 12 | 70 | 38 | ○ |
| 13 | 55 | 0 | × |
| 14 | 55 | 7.5 | ○ |
| 15 | 55 | 15 | ○ |

FIG.7

DIRECTIONALITY OF SHAPING

| SAMPLE | WIRE DIAMETER (μm) | OBLATENESS (%) | JUDGMENT |
|--------|--------------------|----------------|----------|
| 16 | 55 | 23 | ◯ |
| 17 | 55 | 35 | ◯ |
| 18 | 55 | 38 | ◯ |
| 19 | 40 | 0 | ✕ |
| 20 | 40 | 7.5 | ◯ |
| 21 | 40 | 15 | ◯ |
| 22 | 40 | 23 | ◯ |
| 23 | 40 | 35 | ◯ |
| 24 | 40 | 38 | ◯ |
| 25 | 30 | 0 | ✕ |
| 26 | 30 | 7.5 | ✕ |
| 27 | 30 | 15 | ✕ |
| 28 | 30 | 23 | ✕ |
| 29 | 30 | 35 | ✕ |
| 30 | 30 | 38 | ✕ |

FIG.9

ROTATION PERFORMANCE

| SAMPLE | WIRE DIAMETER (μm) | OBLATENESS (%) | JUDGMENT |
|--------|--------|--------|--------|
| 1 | 80 | 0 | O |
| 2 | 80 | 7.5 | O |
| 3 | 80 | 15 | O |
| 4 | 80 | 23 | O |
| 5 | 80 | 35 | × |
| 6 | 80 | 38 | × |
| 7 | 70 | 0 | O |
| 8 | 70 | 7.5 | O |
| 9 | 70 | 15 | O |
| 10 | 70 | 23 | O |
| 11 | 70 | 35 | O |
| 12 | 70 | 38 | O |
| 13 | 55 | 0 | O |
| 14 | 55 | 7.5 | O |
| 15 | 55 | 15 | O |

FIG.10

ROTATION PERFORMANCE

| SAMPLE | WIRE DIAMETER (μm) | OBLATENESS (%) | JUDGMENT |
|--------|--------------------|-----------------|----------|
| 16 | 55 | 23 | ○ |
| 17 | 55 | 35 | ○ |
| 18 | 55 | 38 | ○ |
| 19 | 40 | 0 | ○ |
| 20 | 40 | 7.5 | ○ |
| 21 | 40 | 15 | ○ |
| 22 | 40 | 23 | ○ |
| 23 | 40 | 35 | ○ |
| 24 | 40 | 38 | ○ |
| 25 | 30 | 0 | ○ |
| 26 | 30 | 7.5 | ○ |
| 27 | 30 | 15 | ○ |
| 28 | 30 | 23 | ○ |
| 29 | 30 | 35 | ○ |
| 30 | 30 | 38 | ○ |

GUIDE WIRES

CROSS-REFERENCE TO RELATED APPLICATION

This application is a continuation application of International Application No. PCT/JP2019/051433, filed Dec. 27, 2019, the contents of which are incorporated herein by reference in their entirety.

TECHNICAL FIELD

The devices and techniques disclosed herein generally relate to medical guide wires.

BACKGROUND

Catheters are widely used for treating or inspecting a constricted part or an occluded part (hereinafter referred to as a "lesion") in a blood vessel or the like. Generally, a guide wire is used to guide a catheter to the lesion. A guide wire can include a core shaft formed of a metal material, such as in Patent Literature 1 (JP 2012-91070 A).

In most conventional guide wires, the distal end part of the guide wire has a circular transverse cross-section (a cross section orthogonal to the axial direction of the core shaft).

Currently, in order to improve the vascular selectivity of the guide wire, a procedure called "shaping" may be performed in which an operator such as a doctor bends the distal end part of the guide wire at a predetermined angle before inserting the guide wire into a blood vessel or the like. During this shaping process, the distal end part of a guide wire having a circular transverse cross-section is bent.

SUMMARY

Technical Problem

In some shaping configurations, a bending direction of the distal end part of a guide wire is limited to a predetermined direction (more specifically, a direction along a certain plane along the axial direction of the guide wire, hereinafter referred to as "specific plane direction"). This configuration is sometimes referred to as "two-dimensional shaping." For example, in a shaping procedure in which a first portion—which includes a distal end of a guide wire—and a second portion—which is located closer to a proximal end of the guide wire than the first portion— are each bent, the bending direction of the first and second portions are limited to the same specific plane direction.

In another configuration in which the distal portion of the guide wire has a circular transverse cross-section (taken orthogonal to the axial direction of the core shaft), the deformability of the distal end part of the guide wire does not depend on the deformation direction. Thus, with this configuration, the distal end part of the core shaft (and therefore the distal end part of the guide wire) may be deformed in a direction different from the specific plane direction. This configuration is sometimes referred to as "three-dimensional shaping." However, in this configuration, it is not easy to bend the distal end part of the guide wire in the specific plane direction, or in a direction close to the specific plane direction, during shaping.

The present specification discloses a technique by which it is possible to solve the above-mentioned problems.

Solution to Problem

The techniques and guidewires disclosed can be utilized to solve at least a part of the problem described above, and can be implemented in the following aspects.

In some aspects, an embodiment of the guide wire disclosed herein includes a core shaft having a maximum diameter in a cross section orthogonal to an axial direction of the core shaft and an orthogonal diameter in a direction orthogonal to a direction of the maximum diameter in the cross section, the core shaft including a first specific portion located on a distal portion of the core shaft and having an oblateness between 7% and 35%. In some aspects, the first specific portion extends 5 mm or more in the axial direction. Oblateness is defined as the difference between the maximum diameter and the orthogonal diameter divided by the maximum diameter. As used herein, "diameter" is not limited to a circle and refers to a distance from opposing sides of a surface measured along a straight line passing through a center of the surface.

In some of the present guide wires, the oblateness in the first specific portion is 7% or more. In some such embodiments, the length of the first specific portion in the axial direction is 5 mm or more. The first specific portion can be easily bent in a specific plane direction, such as, for example, in a plane along the axial direction and along a direction of the orthogonal diameter, or a direction close to the specific plane direction.

In some embodiments of the guide wires, as described above, the oblateness of the first specific portion is 35% or less. In some aspects of the guide wires, a rotation performance of the guide wire can be ensured, even when the first specific portion can be easily bent in the specific plane direction in the shaping as described above.

The first specific portion may be formed of a material containing stainless steel. In some such embodiments, the first specific portion is formed of a material containing stainless steel which can easily be plastically deformed. In this way and others, the deformation from the shaping tends to be retained without the first specific portion returning to its original shape, so that it is easy to shape the guide wire.

The core shaft may include a second specific portion located closer to the distal end of the core shaft than the first specific portion and having an oblateness of 40% or more. In some aspects, the present guide wires are particularly suitable in a case where the guide wire is used in a state where the first specific portion is bent to have a relatively small curvature and the second specific portion located closer to the distal end than the first specific portion is bent to have a relatively large curvature.

In some embodiments, a direction of the maximum diameter of the first specific portion and a direction of the maximum diameter of the second specific portion may be parallel to each other. In some aspects, the present guide wires are particularly suitable in a case where the guide wire is used in a state where the first specific portion is bent to have a relatively small curvature and the second specific portion located closer to the distal end than the first specific portion is bent to have a relatively large curvature.

The second specific portion may be formed of a material containing stainless steel. In some such embodiments, the second specific portion is formed of a material containing stainless steel which can easily be plastically deformed. In this way and others, the deformation from the shaping tends to be retained without the second specific portion returning to its original shape, so that it is easy to shape the guide wire.

In some aspects, the core shaft may include a superelastic portion located closer to a proximal end of the guide wire than the first specific portion. The superelastic portion may be formed of a material containing a superelastic alloy. According to this guide wire, the operability and vascular selectivity of the guide wire can be maintained, even when the guide wire has the configuration in which the first specific portion can be easily bent in the specific plane direction in the shaping as described above.

It is noted that the guide wires and techniques disclosed herein can be realized by various aspects, for example, in aspects such as a guide wire and a method of manufacturing the guide wire.

The terms "comprise" and any form thereof such as "comprises" and "comprising," "have" and any form thereof such as "has" and "having," "include" and any form thereof such as "includes" and "including," and "contain" and any form thereof such as "contains" and "containing" are open-ended linking verbs. As a result, a device, like a guide wire, that "comprises," "has," "includes," or "contains" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the devices and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

BRIEF DESCRIPTION OF DRAWINGS

FIG. 6 is a table showing evaluation results of the directionality of shaping in some embodiments of the present guide wires.

FIG. 7 is a table showing evaluation results of the directionality of shaping in some embodiments of present guide wires.

FIG. 9 is a table showing evaluation results of rotation performances in some embodiments of the present guide wires.

FIG. 10 is a table showing evaluation results of rotation performances in some embodiments of the present guide wires.

DETAILED DESCRIPTION OF EMBODIMENTS

Figure 1:
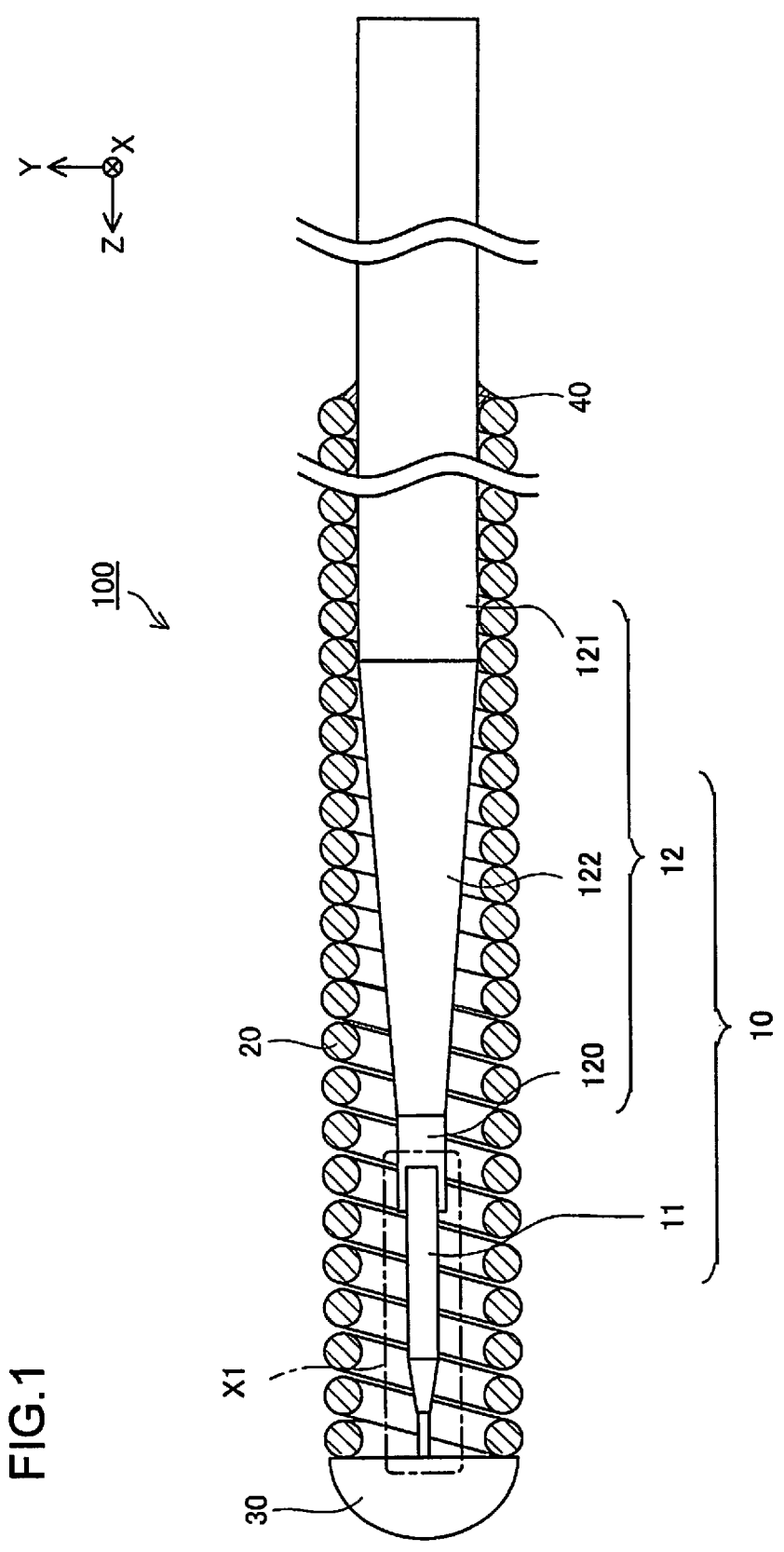
FIG. 1 is a side view of a guide wire in a first embodiment.

FIG. 1 is a side view of a guide wire 100 in a first embodiment. FIG. 1 illustrates XYZ-axes that are orthogonal to each other and illustrates guide wire 100 as seen from an X-axis positive direction. In FIG. 1, a Z-axis corresponds to an axial direction of the guide wire 100. The left side in FIG. 1 is a Z-axis positive direction side and corresponds to a distal end side (far end side) of guide wire 100 that is inserted into a body. The right side of FIG. 1 is a Z-axis negative direction side and corresponds to a proximal end side (near end side) of guide wire 100 that is operated by an operator such as a doctor. The same applies to FIG. 2 and subsequent figures. In FIG. 1, a cross-section (specifically, a YZ cross-section) is illustrated showing a coil body 20 and a distal end-side joint part 30 of guide wire 100, which will be described later. FIG. 1 illustrates a state where the guide wire 100 has a general linear shape substantially parallel to the Z-axis direction. However, the guide wire 100 is sufficiently flexible to be curved. As referenced herein, a portion of guide wire 100 (and its constituent part) including a distal end of the guide wire 100 (and its constituent part) and extending from the distal end toward the proximal end side is referred to as a "distal end part". Additionally, a portion of guide wire 100 (and its constituent part) including a proximal end of the guide wire 100 (and its constituent part) and extending from the proximal end toward the distal end side is referred to as a "proximal end part".

Guide wire 100 is a medical device configured to be inserted into a blood vessel or the like in order to guide a catheter (not illustrated) to a lesion (e.g., a constricted part or occluded part) in the blood vessel or the like. As illustrated in FIG. 1, guide wire 100 includes a core shaft 10, coil body 20, distal end-side joint part 30, and a proximal end-side joint part 40.

Core shaft 10 is a rod-shaped member having a relatively small diameter at a distal end side and a relatively large diameter at a proximal end side. The core shaft 10 includes a first core shaft part 11, which includes the distal end of the core shaft 10, and a second core shaft part 12 located nearer the proximal end side of the core shaft 10 with respect to the first core shaft part 11. The first core shaft part 11 will be described in detail later.

The second core shaft part 12 includes a small diameter portion 120, a large diameter portion 121, and a tapered portion 122. In FIG. 1, a portion of the large diameter portion 121 of the second core shaft part 12 is not illustrated for clarity. The second core shaft part 12 can include or correspond to a superelastic portion. The superelastic portion comprises a material having a superelastic alloy.

The small diameter portion 120 of the second core shaft part 12 is a portion including the distal end of the second core shaft part 12. The small diameter portion 120 has a rod shape having a circular transverse cross-section (e.g., XY cross section) taken orthogonal to the axial direction (e.g., Z-axis direction) of the core shaft 10. As shown in FIG. 1, the axial direction of the core shaft 10 may coincide with (e.g., be coaxial with) the axial direction of the guide wire 100.

The large diameter portion 121 of the second core shaft part 12 is located nearer the proximal end side of the core shaft 10A with respect to the small diameter portion 120. In some embodiments, the large diameter portion 121 has a circular rod shape having a larger outer diameter than the small diameter portion 120 in a transverse cross-section.

The tapered portion 122 of the second core shaft part 12 is disposed between the small diameter portion 120 and the large diameter portion 121. The outer diameter of the tapered portion 122 gradually increases from a boundary position with the small diameter portion 120 to a boundary position with the large diameter portion 121.

It is noted that the shape of the transverse cross-section of each portion of the second core shaft part 12 is not limited to a circular cross-section, and may be shaped in any suitable manner and can include a polygonal cross-section, such as, for example, a triangle or a rectangle.

The second core shaft part 12 can include any suitable material for performing the functions described herein. For example, the second core shaft part 12 can include metal materials, and more specifically, stainless steel (e.g., SUS302, SUS304, SUS316, or the like), superelastic alloys such as Ni—Ti alloys, piano wires, nickel-chromium alloys, cobalt alloys, tungsten, and the like. In the present embodiment, the second core shaft part 12 is formed of a material containing a superelastic alloy such as a Ni—Ti alloy. In some configurations, the second core shaft part 12 formed of a material containing a superelastic alloy, so that a performance (sometimes called "restorability") in which the shape of the second core shaft part 12 returns, after deformation, to the original shape can be exhibited, even when the guide wire 100 advances in a bent blood vessel or the like, thereby making it possible to maintain the operability and vascular selectivity of the guide wire 100.

The coil body 20 is a coil-shaped member and, in some embodiments, can be formed into a hollow cylindrical shape by spirally winding one wire. The coil body 20 is arranged so as to surround the outer periphery of the distal end part of the core shaft 10. For example, coil body 20 may surround the first core shaft part 11 and the small diameter portion 120, the tapered portion 122, and a part of the large diameter portion 121 of the second core shaft part 12.

The coil body 20 can include, for example, a metal material. To elaborate, the metal material can include a radiolucent metal material such as stainless steel (e.g., SUS302, SUS304, SUS316, or the like), a superelastic alloy such as a Ni—Ti alloy, a piano wire, as a nickel-chromium alloy or a cobalt alloy, or a radiopaque metal material such as gold, platinum, tungsten, or an alloy containing these elements, such as, a platinum-nickel alloy. In embodiments in which at least a part of the coil body 20 is a radiopaque material, an operator can identify the position of the coil body 20 in a radiolucent image.

The distal end-side joint part 30 couples the distal end of the core shaft 10 to the distal end of the coil body 20. The distal end of the core shaft 10 and the distal end of the coil body 20 can be fixed to, or be embedded in, the distal end-side joint part 30. The outer peripheral surface on the distal end side of the distal end-side joint part 30 can be a smooth surface, such as, for example, a substantially hemispherical surface. The distal end-side joint part 30 can be formed of a metal solder (e.g., silver solder, gold solder, zinc, Sn—Ag alloy, and Au—Sn alloy) or a bonding agent such as an epoxy adhesive. By arranging the distal end-side joint part 30 on the distal end side with respect to the core shaft 10, it is possible to prevent the core shaft 10 from contacting a blood vessel wall or the like. In this way and others, guide wire 10 can prevent the core shaft 10 from being damaged.

The proximal end-side joint part 40 couples a proximal end side of the core shaft 10 to a proximal end side of the coil body 20. The proximal end-side joint part 40 can be formed of the same material as the distal end-side joint part 30, described above. It is noted that the position of the proximal end-side joint part 40 is not limited to the proximal end side of the coil body 20, and may be located at any suitable position along the coil body 20.

Figure 2:
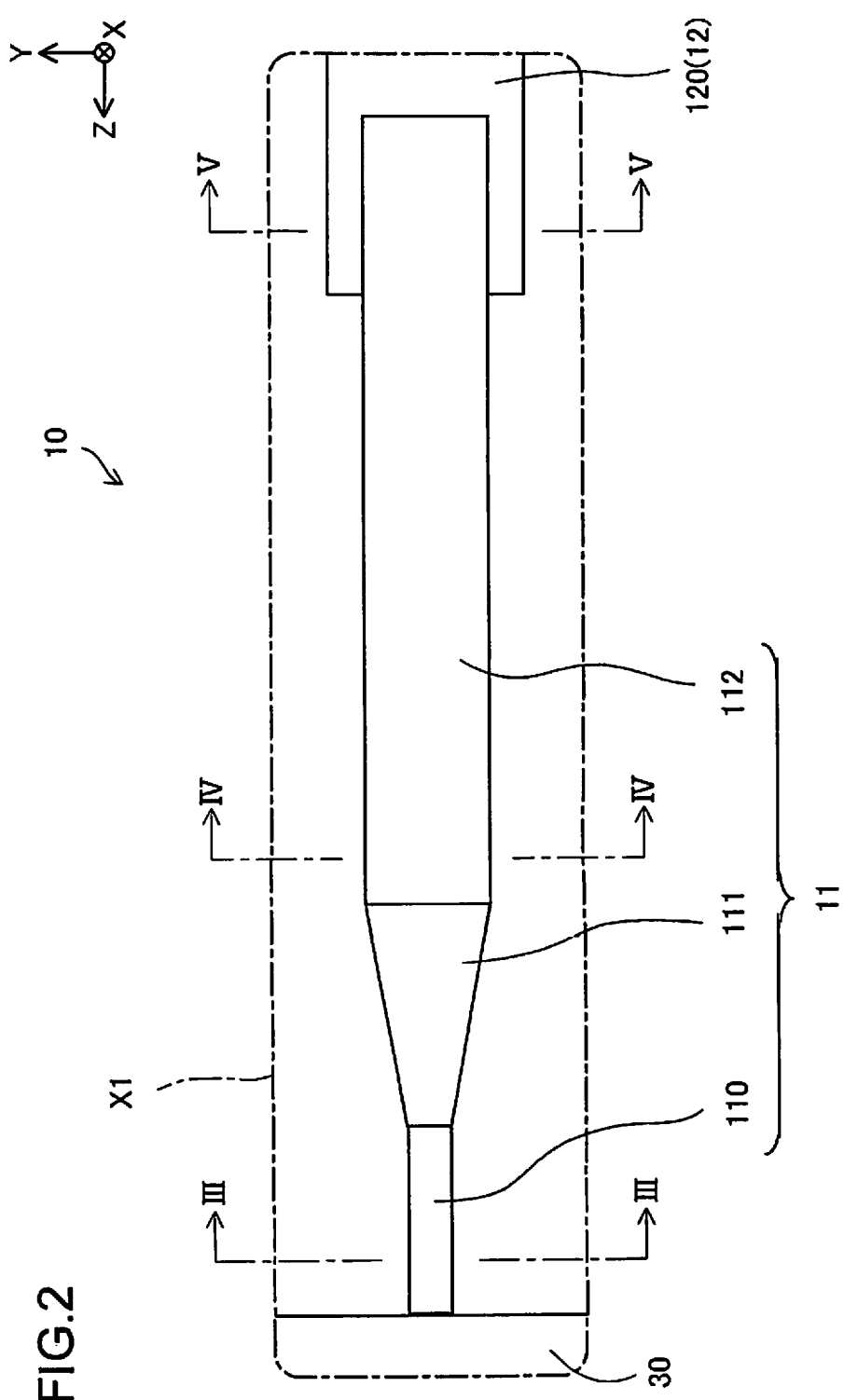
FIG. 2 is an enlarged side view of a core shaft of the guide wire shown in FIG. 1.
Figure 3:
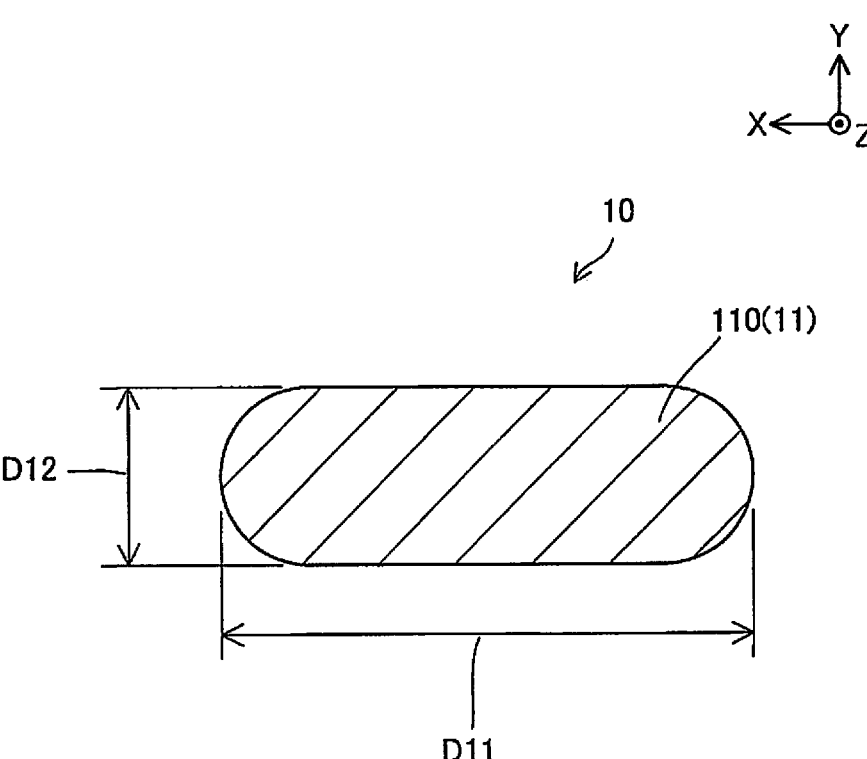
FIG. 3 is a cross-sectional view of the core shaft taken along line of FIG. 2.
Figure 4:
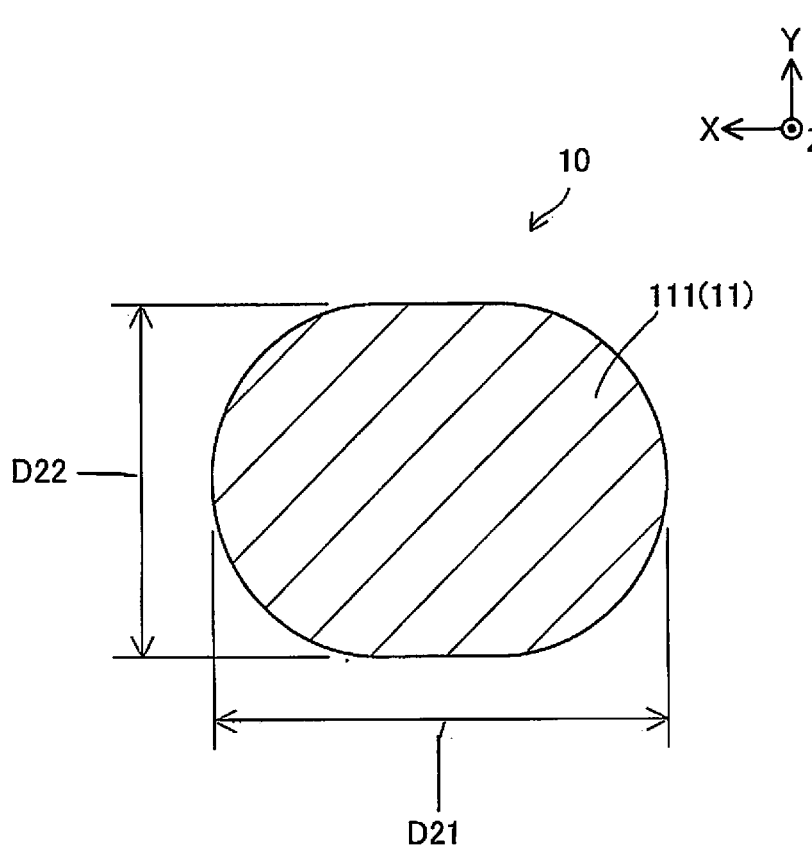
FIG. 4 is a cross-sectional view of the core shaft taken along line IV-IV of FIG. 2.
Figure 5:
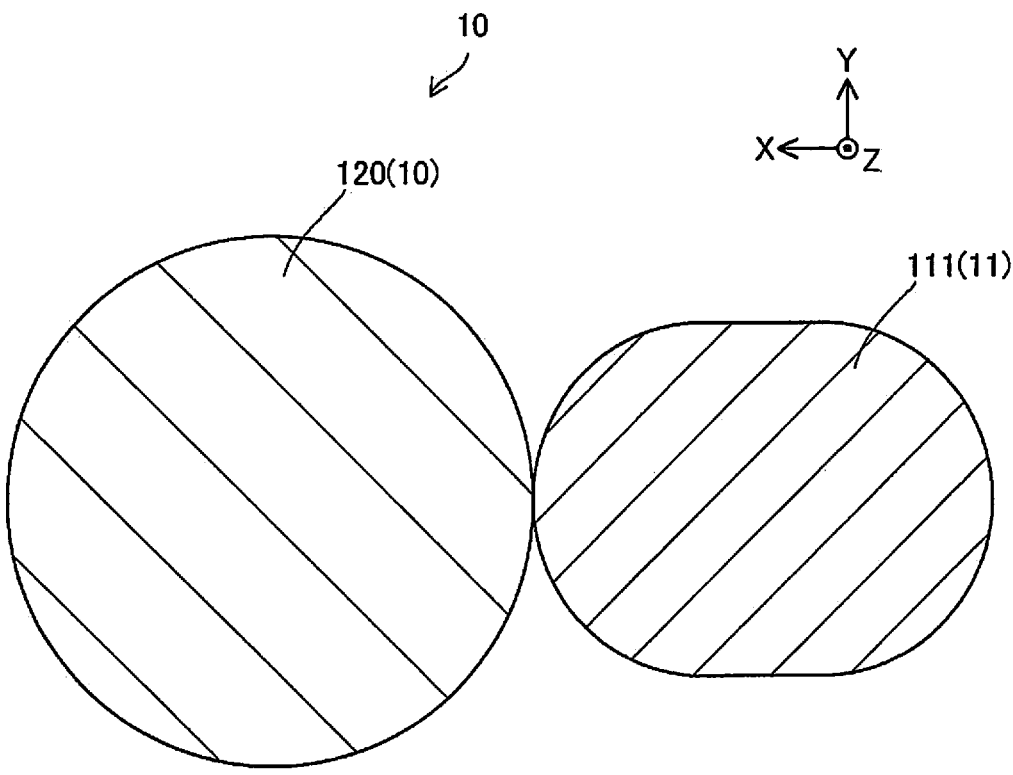
FIG. 5 is a cross-sectional view of the core shaft taken along line V-V of FIG. 2.

FIG. 2 is an enlarged side view of the core shaft 10. FIG. 2 illustrates the part of the core shaft 10 (the portion within box X1 in FIG. 1) seen from the X-axis positive direction. FIG. 3 shows a transverse cross-section of the core shaft 10 at a position of FIG. 2, FIG. 4 shows a transverse cross-section of the core shaft 10 at a position IV-IV of FIG. 2, and FIG. 5 shows a transverse cross-section of the core shaft 10 at a position V-V of FIG. 2. FIG. 3 to FIG. 5 illustrate a transverse cross-section of the core shaft 10 seen from the Z-axis negative direction.

The first core shaft part 11 can be a rod-shaped member. In the embodiment shown, the first core shaft part 11 includes a material containing stainless steel (e.g., SUS302, SUS304, SUS316, or the like). The first core shaft part 11 is sometimes referred to as "ribbon" or "shaping ribbon". The first core shaft part 11 can be connected to the distal end of (the small diameter portion 120 of) the second core shaft part 12. For example, in some embodiments first core shaft part 11 is bonded with small diameter portion by a metal solder such as silver solder, gold solder, zinc, a Sn—Ag alloy, or an Au—Sn alloy, or by an adhesive such as an epoxy adhesive.

As illustrated in FIG. 2, the first core shaft part 11 includes a strongly oblate part 110, a slightly oblate part 112, and a tapered portion 111. The strongly oblate part 110 of the first core shaft part 11 may correspond to the second specific portion as recited herein, and the slightly oblate part 112 of the first core shaft part 11 may correspond to the first specific portion as recited herein.

In the following, the longest diameter in a transverse cross-section, such as the XY cross-section, orthogonal to the axial direction of the core shaft 10 (e.g., Z-axis direction) is referred to as "maximum diameter." The diameter in a direction orthogonal to a direction of the maximum diameter in the transverse cross-section is referred to as "orthogonal diameter," and a value (%) obtained by dividing the difference between the maximum diameter and the orthogonal diameter by the maximum diameter is referred to as "oblateness."

The strongly oblate part 110 of the first core shaft part 11 includes the distal end of the first core shaft part 11.

As illustrated in FIG. 3, the transverse cross-section of the strongly oblate part 110 has an oblate or elongated shape (a substantially rectangular or substantially elliptical shape) having a diameter in the X-axis direction that is greater than a diameter in the Y-axis direction. In the transverse cross-section of the strongly oblate part 110, the diameter in the X-axis direction (long diameter) corresponds to a maximum diameter D11 and the diameter in the Y-axis direction (small diameter) corresponds to an orthogonal diameter D12.

The strongly oblate part 110 of the first core shaft part 11 may have an oblateness of 40% or more in the transverse cross-section. To illustrate, first core shaft part 11 may be formed from a rod-shaped member, such as a wire, that is flattened (e.g., by press working or the like). As a specific example, for a wire diameter of a rod-shaped member before flattening of 40 μm, the maximum diameter D11 is 57 μm, the orthogonal diameter D12 is 24 μm, and the oblateness is 57.9% in the strongly oblate part 110. However, the oblateness of the strongly oblate part 110 of the first core shaft part 11 in the transverse cross-section may be any other value of 40% or more (the same applying to a third embodiment described below).

As illustrated in FIG. 2, the slightly oblate part 112 of the first core shaft part 11 includes the proximal most end of the first core shaft part 11. The slightly oblate part 112 includes a connection portion connecting to the distal end part of the second core shaft part 12 (e.g., small diameter portion 120).

As illustrated in FIG. 4, the transverse cross-section of the slightly oblate part 112 has an oblate or elongated shape (e.g., a substantially rectangular or substantially elliptical shape) having a diameter in the X-axis direction (long diameter) that is greater than a diameter in the Y-axis direction (small diameter). In the transverse cross-section of the slightly oblate part 112, the long diameter corresponds to a maximum diameter D21 and the small diameter corresponds to an orthogonal diameter D22.

The oblateness of the slightly oblate part 112 of the first core shaft part 11 can be between 7% and 35%. As a specific example, for an unflattened wire diameter of 40 μm, when the oblateness is 30.0%, the maximum diameter D21 is 46 μm and the orthogonal diameter D22 is 32 μm in the slightly oblate part 112. For the same wire, when the oblateness is 7.3%, the maximum diameter D21 is 41 μm and the orthogonal diameter D22 is 38 μm. For an unflattened wire diameter of 75 μm, when the oblateness is 31.0%, the maximum diameter D21 is 87 μm and the orthogonal diameter D22 is 60 μm, and when the oblateness is 7.8%, the maximum diameter D21 is 77 μm and the orthogonal diameter D22 is 71 μm.

As illustrated in FIG. 2, the tapered portion 111 of the first core shaft part 11 is disposed between the strongly oblate part 110 and the slightly oblate part 112. The oblateness of the tapered portion 111 changes in a stepwise manner, or gradually changes, from a boundary position adjacent with the strongly oblate part 110 to a boundary position adjacent with the slightly oblate part 112.

The first core shaft part 11 having a transverse cross-section with an oblate shape (a substantially rectangular or substantially elliptical shape) described above can include, for example, a material containing stainless steel, and can be manufactured by flattening a rod-shaped member having a circular transverse cross-section in a suitable manner, such as via press working.

As described above, the guide wire 100 of the first embodiment includes the core shaft 10. The core shaft 10 includes the slightly oblate part 112 (of the first core shaft part 11) that is located on the distal end side of the core shaft 10 and has an oblateness between 7% and 35%. The length of the slightly oblate part 112 of the first core shaft part 11 in the axial direction of the core shaft 10 (e.g., Z-axis direction) can be 5 mm or more.

Contrary to traditional guidewires with circular cross-sections, the guide wire 100 includes the slightly oblate part 112 of the first core shaft part 11 having an oblateness of 7% or more, as described above. In some embodiments, the length of the slightly oblate part 112 of the first core shaft part 11 in the axial direction of the core shaft 10 is 5 mm or more. Thus, in the guide wire 100, as compared with the configuration in which the slightly oblate part 112 of the first core shaft part 11 has a circular transverse cross-section (in other words, an oblateness of 0%), the bending direction of the slightly oblate part 112 can be biased to the specific plane direction (e.g., a direction along the YZ plane along the axial direction of the core shaft 10 and along the direction of the orthogonal diameter D22) in the shaping. Thus, for the guide wire 100, the slightly oblate part 112 of the first core shaft part 11 can be easily bent in the specific plane direction (or a direction close to the specific plane direction) in the shaping.

Configurations where the slightly oblate part 112 of the first core shaft part 11 has an oblateness of 40% or more may result in "whipping" which may reduce the rotation performance (operability) of the guide wire 100. During whipping, when the guide wire 100 is rotated within a blood vessel, the distal end part of the guide wire 100 bounces and escapes in any direction like a whip.

On the other hand, in the guide wire 100, the oblateness of the slightly oblate part 112 of the first core shaft part 11 can be less than or equal to 35%. In this way and others, in the guide wire 100, the occurrence of whipping is prevented when the guide wire 100 is rotated within a blood vessel, and therefore the rotation performance of the guide wire 100 is not impacted due to the whipping. Thus, the rotation performance of the guide wire 100 can be maintained, even when the slightly oblate part 112 of the first core shaft part 11 can be easily bent in the specific plane direction in the shaping process.

In a configuration in which the length of the slightly oblate part 112 of the first core shaft part 11 in the axial direction of the core shaft 10 is less than 5 mm, it can be difficult to shape the distal end part. In the present embodiments, the length of the slightly oblate part 112 of the first core shaft part 11 in the axial direction of the core shaft 10 can be 5 mm or more, and thus, it is easy to shape the distal end part. However, if the length of the slightly oblate part 112 is excessively long, whipping may occur. Therefore, the length of the slightly oblate part 112 of the first core shaft part 11 in the axial direction of the core shaft 10 is preferably, for example, 15 mm or less.

In the guide wire 100, the wire diameter of the slightly oblate part 112 of the first core shaft part 11 can be 40 μm or more. In configurations in which the wire diameter is less than 40 μm, the directionality of shaping is unlikely to be limited to the specific plane direction, regardless of the oblateness. Thus, in the present embodiment in which the wire diameter of the slightly oblate part 112 of the first core shaft part 11 is 40 μm or more, the directionality of shaping tends to be limited to the specific plane direction, as compared with the configuration in which the wire diameter is less than 40 μm. In this way and others, the rotation performance of the guide wire 100 can be better controlled.

In the guide wire 100, the slightly oblate part 112 of the first core shaft part 11 can include a material containing stainless steel. Stainless steel can be plastically deformed more easily than some other materials, and thus, the deformation from the shaping tends to be retained without the guide wire 100 returning to its original shape, so that the slightly oblate part 112 can easily be shaped.

The strongly oblate part 110 of the first core shaft part 11, which is located closer to the distal end of the core shaft 10 than the slightly oblate part 112 of the first core shaft part 11, can have an oblateness of 40% or more. The bending angle from the shaping of the strongly oblate part 110 is likely to be larger than the bending angle from the shaping of the slightly oblate part 112 of the first core shaft part 11. Therefore, the guide wire 100 can be suitable in a case where the guide wire 100 is used in a state where the slightly oblate part 112 of the first core shaft part 11 is bent to have a relatively small curvature and the strongly oblate part 110 is bent to have a relatively large curvature.

In the guide wire 100, the direction of the maximum diameter D21 of the slightly oblate part 112 of the first core shaft part 11 and the direction of the maximum diameter D11 of the strongly oblate part 110 of the first core shaft part 11 can be parallel to each other. Bending directions from the shaping of the slightly oblate part 112 and the strongly oblate part 110 of the first core shaft part 11 tend to be along the orthogonal diameters D12 and D22 rather than the directions of the maximum diameters D11 and D21, and thus, the bending directions can be substantially the same plane direction. In this way and others, it is possible to prevent the occurrence of three-dimensional shaping between the slightly oblate part 112 and the strongly oblate part 110 of the first core shaft part 11, so that the directionality of deformation of the guide wire 100 from the shaping can be limited to the specific plane direction (or a direction close to the specific plane direction).

In the guide wire 100, the strongly oblate part 110 of the first core shaft part 11 can be formed of a material comprising stainless steel. Stainless steel can be plastically deformed more easily than other materials, and thus, the deformation from the shaping tends to be retained without the guide wire 100 returning to its original shape, so that the strongly oblate part 110 can be easily shaped.

The second core shaft part 12 can be formed of a material containing a superelastic alloy. In some such configurations, the restorability of the second core shaft part 12 can be improved, thereby providing the desired operability and vascular selectivity in the guide wire 100. In this way and others, guide wire 100 can have sufficient operability and vascular selectivity, even when the slightly oblate part 112 of the first core shaft part 11 can be easily bent in the specific plane direction in the shaping process.

FIGS. 6 and 7 show diagrams illustrating evaluation results of the directionality of shaping for several samples of guide wires made according to the described embodiments.

As shown in FIGS. 6 and 7, the directionality of shaping was evaluated for thirty samples of guide wires. Each sample has substantially the same configuration as the guide wire 100 described above. Specifically, each sample included a core shaft 10 and a coil body 20. The core shaft 10 includes a first core shaft part 11 including a distal end of the core shaft and being formed of a material containing stainless steel and a second core shaft part 12 located proximal to the first core shaft part and formed of a material containing a superelastic alloy, such as a Ni—Ti alloy.

The thirty samples differ from one another in at least any one of the wire diameter (the longest diameter in the transverse cross-section (XY cross section)) and the oblateness. As shown, samples 1 to 6 have a wire diameter of 80 μm, samples 7 to 12 have a wire diameter of 70 μm, samples 13 to 18 have a wire diameter of 55 μm, samples 19 to 24 have a wire diameter of 40 μm, and samples 25 to 30 have a wire diameter of 30 μm.

As shown in FIG. 6, samples 1 to 6 differ from one another in oblateness. Specifically, sample 1 has an oblateness of 0% (e.g., circular cross-section), sample 2 has an oblateness of 7.5%, sample 3 has an oblateness of 15%, sample 4 has an oblateness of 23%, sample 5 has an oblateness of 35%, and sample 6 has an oblateness of 38%. Similarly, samples 7 to 12, samples 13 to 18, samples 19 to 24, and samples 25 to 30 respectively differ from one another in oblateness, as shown in FIGS. 6 and 7.

The maximum diameter and the orthogonal diameter (and therefore the oblateness) in each sample can be adjusted by changing the pressing amount of a press used when manufacturing the first core shaft part from a wire having a circular transverse cross-section. Specifically, when the pressing amount of the press is increased, the oblateness can be increased, with the maximum diameter being increased and the orthogonal diameter being decreased.

The maximum diameter and the orthogonal diameter in each sample shown in FIGS. 6 and 7 were determined using the following process. First, the core shaft of each sample is cut out, and the resulting cut surface is identified by observation with an electron microscope (e.g., using a magnification of 100,000 times). The maximum diameter and the orthogonal diameter were each taken at a plurality of different locations (for example, 10 locations) in the first core shaft part and an average value of the maximum diameters at the plurality of locations was calculated and defined as the maximum diameter of the first core shaft part. Similarly, an average value of the orthogonal diameters at the plurality of locations was calculated and defined as the orthogonal diameter of the first core shaft part. The measurement method is not limited to this particular process and alternative measurement methods may be used, such as for example, a method of irradiating the outer periphery of the core shaft with a laser to extract the outer shape of the core shaft to calculate the maximum diameter and the orthogonal diameter.

Figure 8:
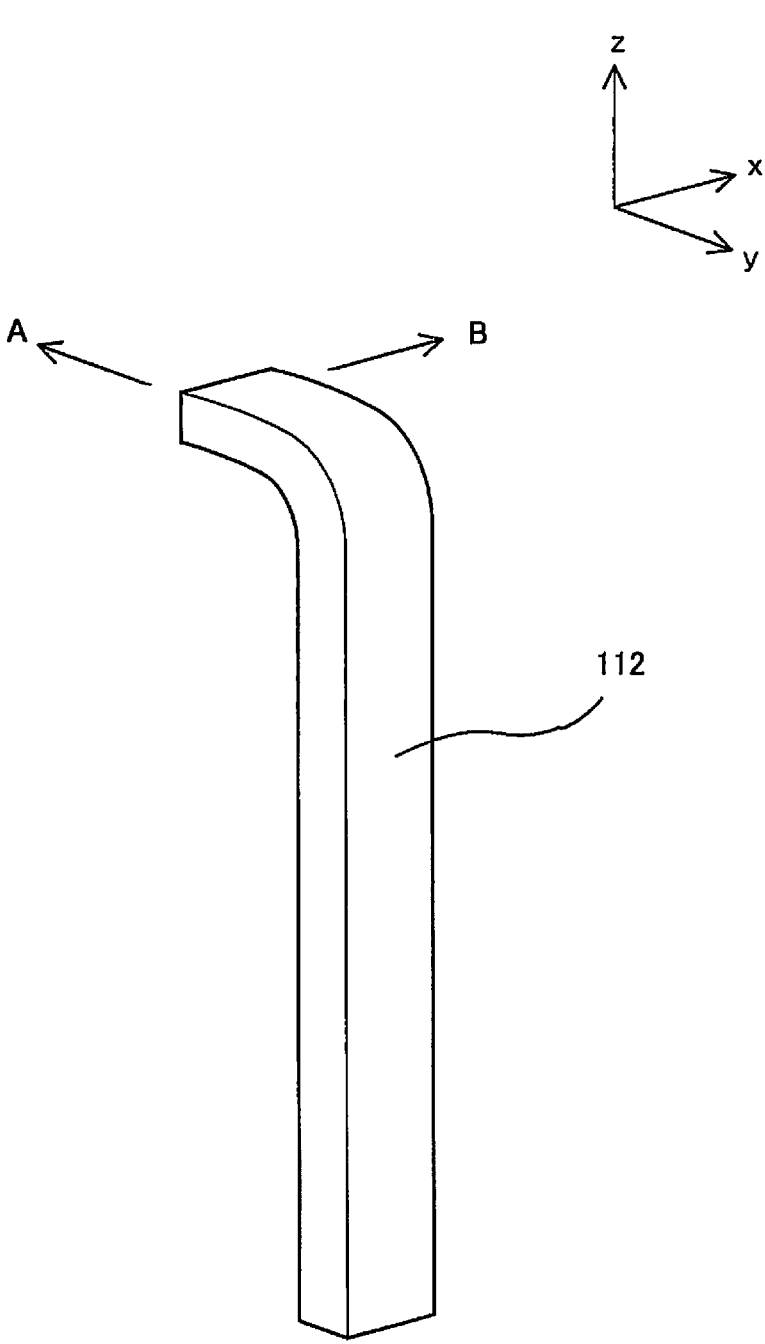
FIG. 8 is diagram of a portion of a guide wire for measuring the directionality of shaping.

FIG. 8 illustrates the slightly oblate part 112 of a sample of the present embodiments. The directionality of shaping was determined using the following process. First, as illustrated in FIG. 8, the distal end of the first core shaft part is curved at an angle of 90° along a plane direction A along the direction of the orthogonal diameter (e.g., along the YZ plane). Next, a force is applied to the distal end of the first core shaft part along a plane direction B that is substantially orthogonal to the plane direction A. While the force was applied in direction B, the sample was evaluated. During evaluation, when the distal end of the first core shaft part extended in the plane direction A (or a plane direction closer to the plane direction A than the plane direction B), the sample was judged as "good" ("0" in the Judgment column of FIGS. 6 and 7), and when the distal end of the first core shaft part was curved in the plane direction B (or a plane direction closer to the plane direction B rather than the plane direction A), the sample was judged as "poor" ("x" in the Judgment column in FIGS. 6 and 7).

As illustrated in FIGS. 6 and 7, in samples 1, 7, 13, and 19, the evaluation results of the directionality of shaping were "poor." On the other hand, in samples 2 to 6, 8 to 12, 14 to 18, and 20 to 24, the evaluation results of the directionality of shaping were "good." This shows that, when the oblateness is 7% or more, the directionality of shaping tends to be limited to the specific plane direction (the plane direction A along the direction of the orthogonal diameter).

In samples 25 to 30, the evaluation results of the directionality of shaping were "poor." On the other hand, as described above, in samples 20 to 24, the evaluation results of the directionality of shaping were "good." This shows that, when the wire diameter is less than 40 μm, the directionality of shaping is unlikely to be limited to the specific plane direction, regardless of the oblateness.

Figure 11:
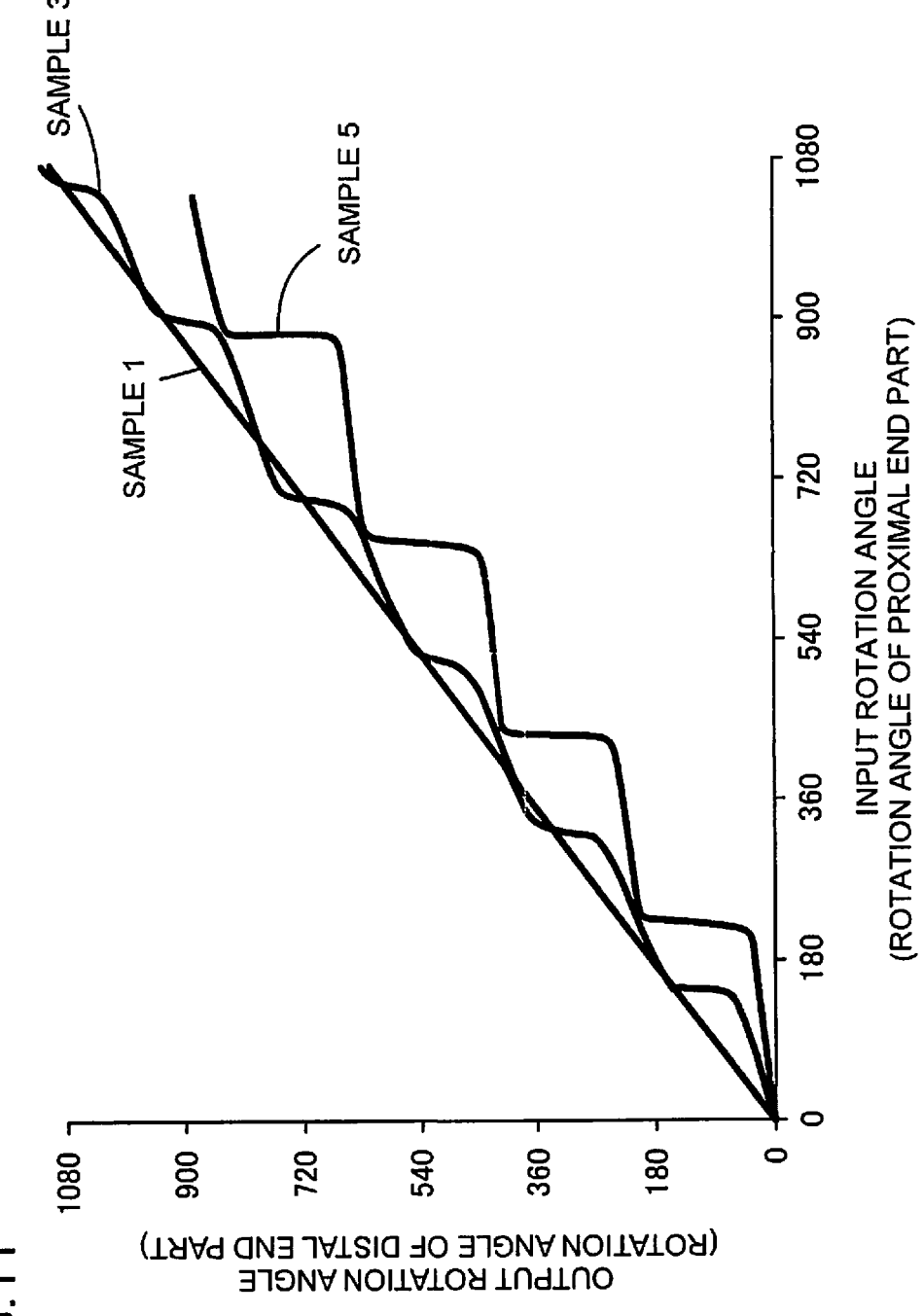
FIG. 11 is a graph showing an example of measurement results of the directionality of shaping in some embodiments of the present guide wires.

FIGS. 9 and 10 show tables of the evaluation results of the rotation performance of the thirty samples described above with reference to FIGS. 6 and 7. FIG. 11 is a graph showing an example of measurement results of the rotation performance of some of the samples.

The rotation performance was evaluated using the following process. The proximal end part of the guide wire is rotated (in the circumferential direction of the axis of the guide wire), and it is evaluated whether t the distal end part (e.g., the first core shaft part) of the guide wire rotates, before the proximal end part of the guide wire is rotated by 180°.

Figure 12:
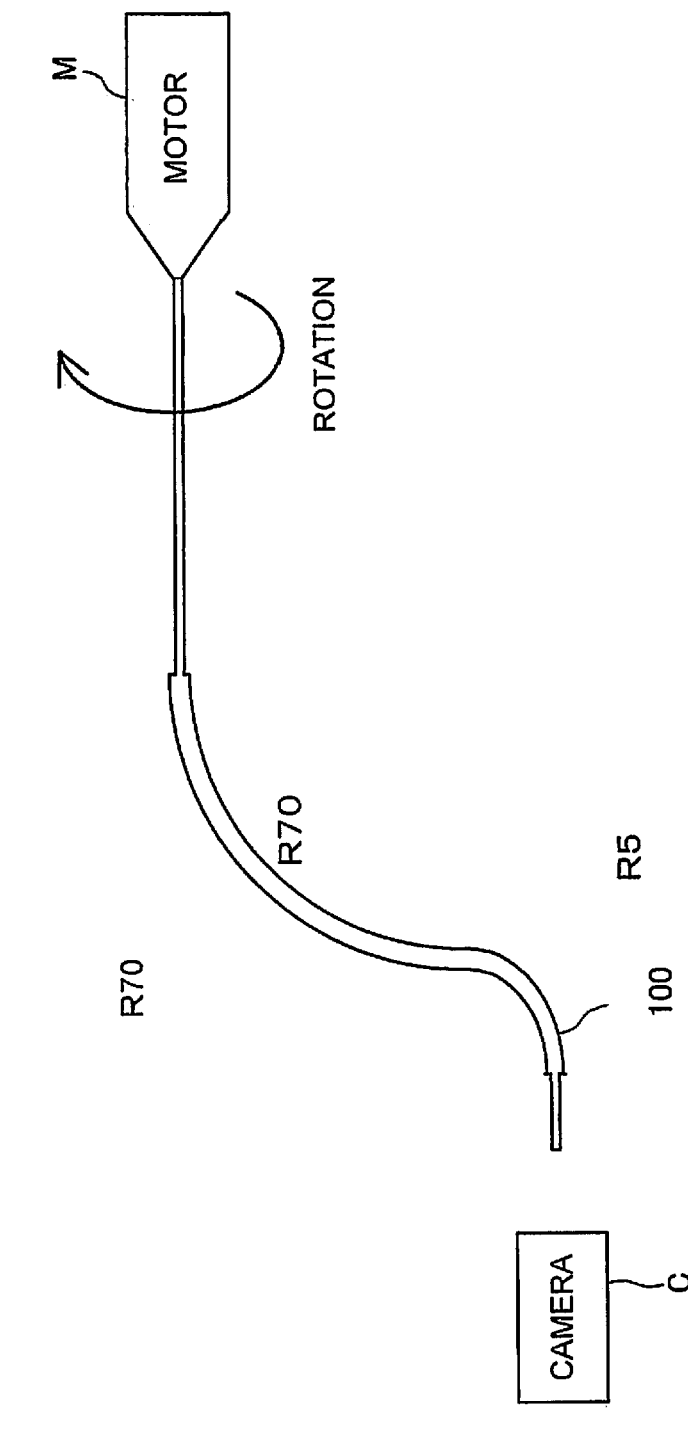
FIG. 12 is a diagram of an example of a system used for measuring the rotation performance.

FIG. 12 shows a diagram of a system used for measuring the rotation performance. Specifically, as illustrated in FIG. 12, a guide wire 100 in which the distal end part of the first core shaft part (e.g., the slightly oblate part 112) is curved at 90° with a radius of curvature of 5 mm (R5) is utilized, and a proximal portion at the proximal end side thereof is curved to a side opposite to the distal end part with a radius of curvature of 70 mm (R70). A motor M for rotating the guide wire (in the circumferential direction of the axis of the guide wire) is attached to the proximal end part of the guide wire. Subsequently, the motor M is driven to rotate the guide wire (in the circumferential direction of the axis of the guide wire). At this time, images of the distal end part of the guide wire is captured using a camera C, and it is determined whether or not the distal end part of the guide wire rotated.

When it is determined that the distal end part of the guide wire 100 rotates before the proximal end part rotates by 180°, the sample was judged as "good" ("0" in the Judgment column of FIGS. 9 and 10). However, if the distal end part of the guide wire does not rotate before the proximal end part rotates 180°, the sample was judged as "poor" ("x" in the Judgment column in FIGS. 9 and 10). When the radius of curvature at the distal end part of the first core shaft part is small, the delay in the rotation angle of the distal end part with respect to the rotation angle of the proximal end part tends to increase, and therefore, the pass/fail criteria for evaluation of the rotation performance differs depending on the radius of curvature at the distal end part of the first core shaft part.

As shown in FIGS. 9 and 10, the evaluation results of the rotation performance were "good" for samples 1 to 4. On the other hand, the evaluation results of the rotation performance were "poor" for samples 5 and 6. This shows that the rotation performance of the guide wire is improved by setting the oblateness to less than 35%. It is considered that the reason why the rotation performance of the guide wire is improved is that the sufficiently small oblateness prevents the occurrence of whipping, as illustrated in FIG. 11.

FIG. 11 indicates the measurement results of samples 1, 3, and 5 as examples of the measurement results of the rotation performance of the guide wire in this performance evaluation. In sample 1, an input rotation angle (rotation angle of the proximal end part of the guide wire) and an output rotation angle (rotation angle of the distal end part of the guide wire) have a substantially linear relationship with an inclination close to 1. In other words, for sample 1, when the proximal end part of the guide wire is rotated, the distal end part rotates by a substantially similar rotation angle. Therefore, in sample 1, the distal end part of the guide wire rotates before the proximal end part rotates by 180°, and thus, sample 1 was judged as "good." In sample 3, the distal end part rotates before the proximal end part rotates by a rotation angle smaller than 180°, and thus, sample 3 was judged as "good." In sample 5, the distal end part rotates only until the proximal end part rotates by a rotation angle larger than 180°, and thus, sample 5 was judged as "poor."

In samples 7 to 30, the evaluation results of the rotation performance were "good." This means that, in a wire diameter of less than 80 μm, rotation performance is less impacted by oblateness, and the problem with rotation performance as described above is likely to occur in a wire diameter of 80 μm or more.

The results of the performance evaluation (both directionality of shaping and the rotation performance) in other embodiments and modifications of the present guidewires, which will be described later, are similar to the results of the performance evaluation in the guide wire 100.

Figure 13:
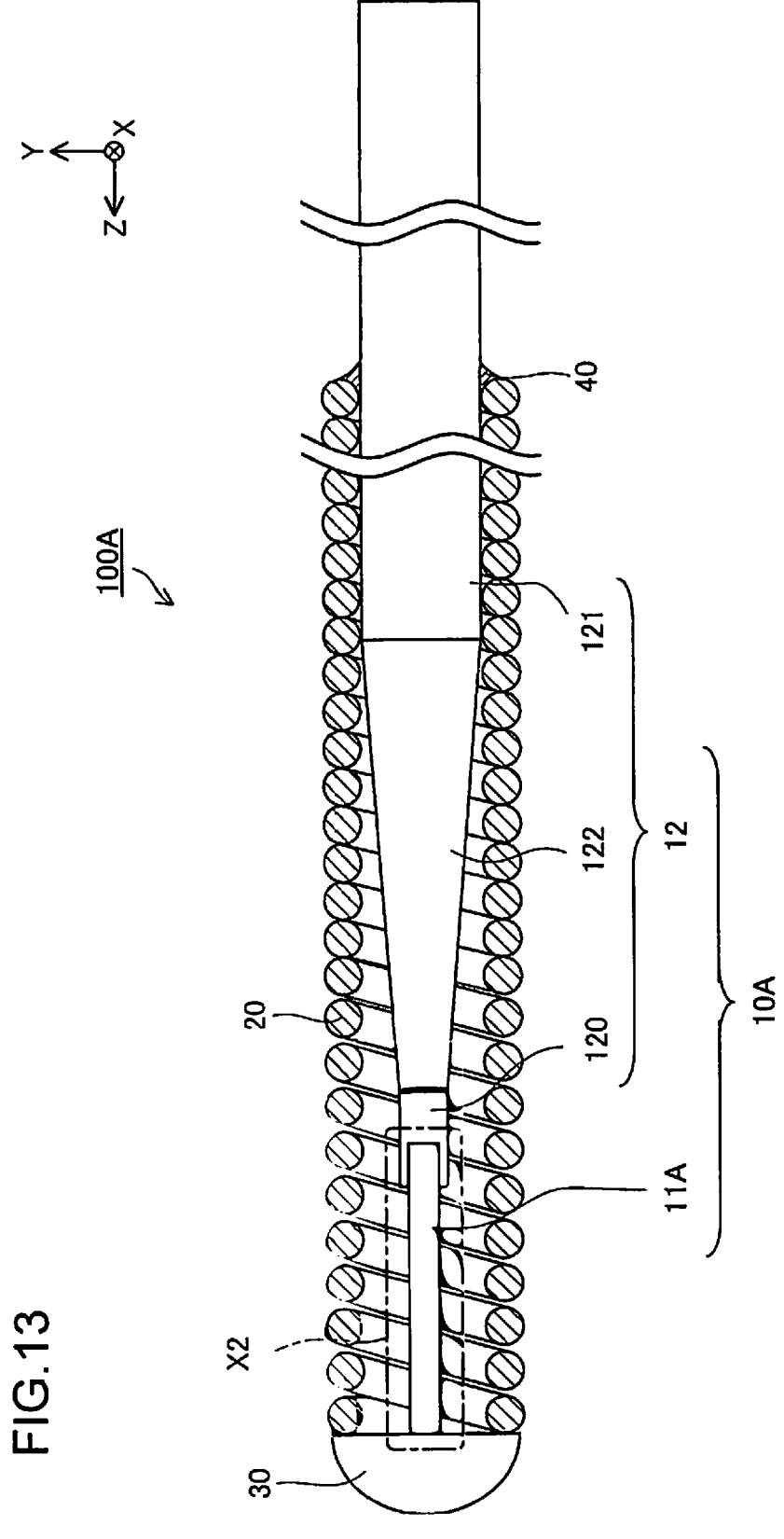
FIG. 13 is a side of a guide wire in a second embodiment.
Figure 14:
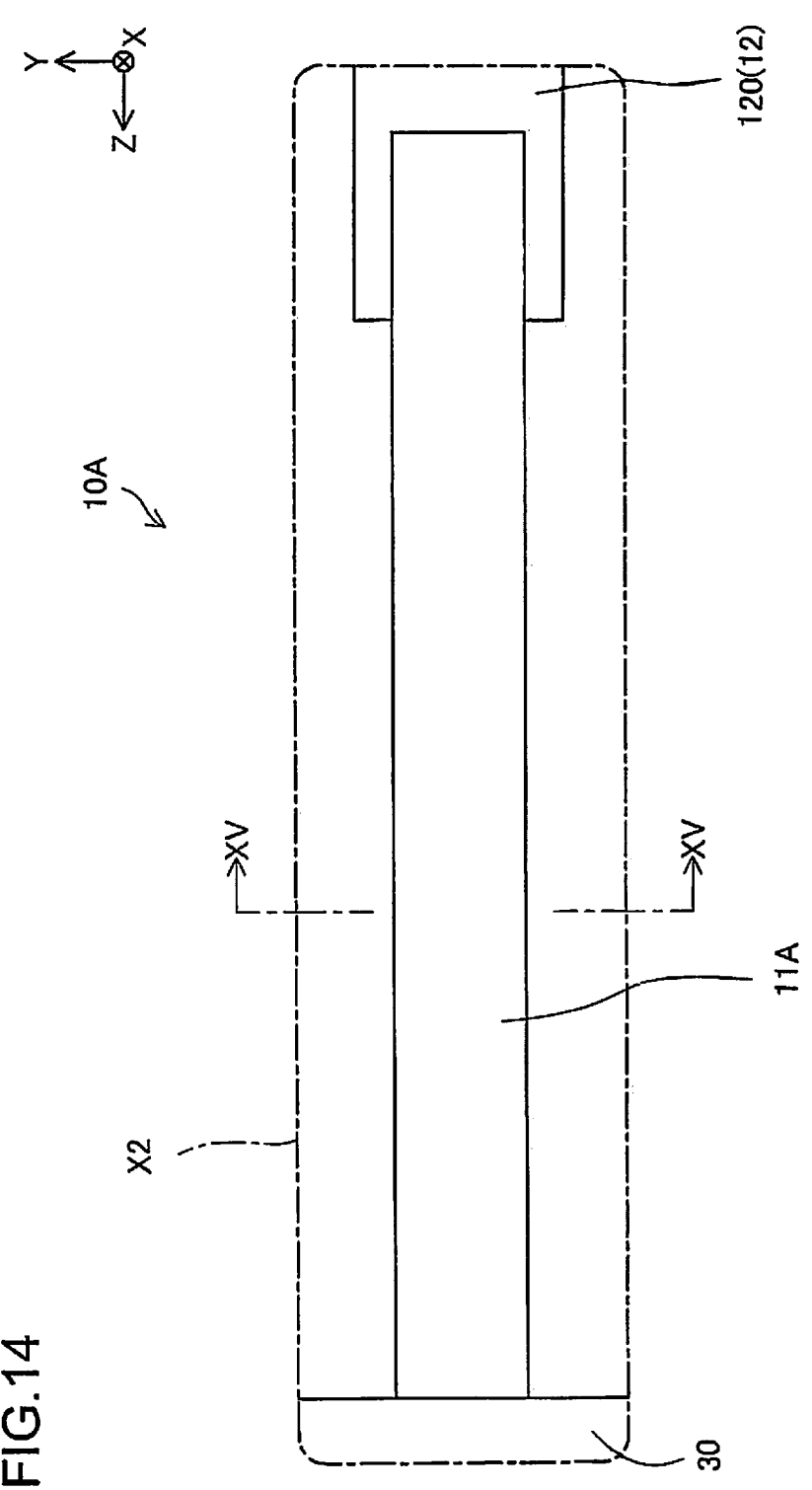
FIG. 14 is an enlarged side view of a core shaft of the guide wire shown in FIG. 13.
Figure 15:
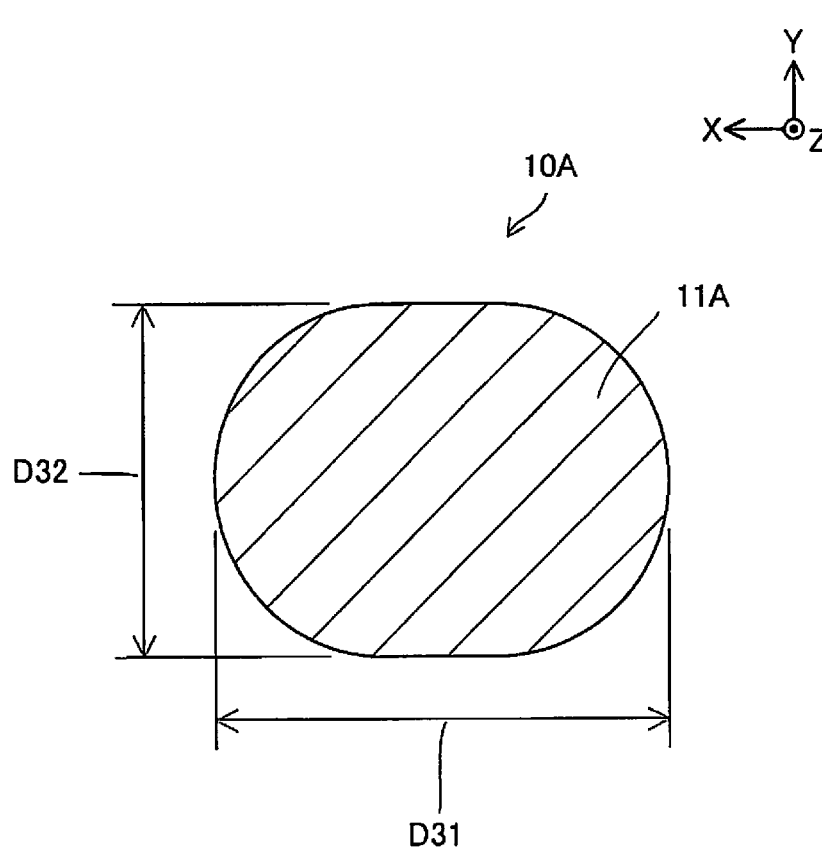
FIG. 15 is a cross-sectional view of the core shaft taken along line XV-XV of FIG. 14.

FIG. 13 is a side view of a guide wire 100A in a second embodiment. FIG. 13 illustrates the guide wire 100A seen from the X-axis positive direction. FIG. 14 is an enlarged side view of a core shaft 10A of guide wire 100A. For example, FIG. 14 illustrates a part of the core shaft 10A (the portion within box X2 in FIG. 13) seen from the X-axis positive direction. FIG. 15 shows a cross-sectional view of the core shaft 10A at a position XV-XV of FIG. 14. Specifically, FIG. 15 illustrates the transverse cross-section of the core shaft 10A seen from the Z-axis negative direction.

As illustrated in FIGS. 13 and 14, the guide wire 100A differs from the guide wire 100, described above, in the shape of a first core shaft part 11A. In the following, components of the guide wire 100A that are the same as those of the guide wire 100 will be referred to by the same reference numerals, and description thereof will be omitted where appropriate.

As illustrated in FIGS. 13 and 14, the core shaft 10A includes the first core shaft part 11A including the distal end of the core shaft 10A and a second core shaft part 12 located proximal to the first core shaft part 11A.

As illustrated in FIG. 15, the transverse cross-section of the first core shaft part 11A (e.g., XY cross section) has an oblate or elongated shape (e.g., a substantially rectangular or substantially elliptical shape) with a diameter in the X-axis direction (long diameter) that is greater than a diameter in the Y-axis direction (small diameter). In the transverse cross-section of the first core shaft part 11A, the long diameter corresponds to a maximum diameter D31 (e.g., the longest diameter in a cross section orthogonal to the axial direction of the core shaft 10A), and the small diameter corresponds to an orthogonal diameter D32 (e.g., the longest diameter in a direction orthogonal to the direction of the maximum diameter in a cross section orthogonal to the axial direction of the core shaft 10A).

The first core shaft part 11A is a rod-shaped member. The oblateness in the first core shaft part 11A can be between 7% and 35%. As a specific example, for a wire diameter of 40 μm of the first core shaft part 11A, when the oblateness is 30.0%, the maximum diameter D31 is 46 μm and the orthogonal diameter D32 is 32 μm. When the oblateness is 7.3%, the maximum diameter D31 is 41 μm and the orthogonal diameter D32 is 38 μm. However, the oblateness in the first core shaft part 11A may be any other value between 7% and 35%. When the wire diameter is changed, the maximum diameter D31 and the orthogonal diameter D32 are similar to those described in guide wire 100. The first core shaft part 11A can include or correspond to the first specific portion.

The shape of the transverse cross-section of the first core shaft part 11A may be uniform over the entire length of the first core shaft part 11A in the axial direction (e.g., Z-axis direction).

As described above, the guide wire 100A includes the core shaft 10A. The core shaft 10A includes the first core shaft part 11A, which is located on the distal end side of the core shaft 10A and has an oblateness between 7% and 35%.

The length of the first core shaft part 11A in the axial direction of the core shaft 10A (e.g., Z-axis direction) may be 5 mm or more.

In the guide wire 100A, the bending direction of the first core shaft part 11A tends to be limited to the specific plane direction (e.g., a direction along the YZ plane along the axial direction of the core shaft 10A and along the direction of the orthogonal diameter D32) in the shaping process. Thus, the first core shaft part 11A can be easily bent in the specific plane direction (or a direction close to the specific plane direction) in the shaping process. In addition, in the guide wire 100A of the second embodiment, the oblateness of the first core shaft part 11A can be less than 35%. Thus, according to this guide wire 100A of the second embodiment, for the same reason as in the case of the guide wire 100, the rotation performance of the guide wire 100A can be maintained, even when the guide wire 100A has the configuration in which the first core shaft part 11A can be easily bent in the specific plane direction in the shaping as described above.

In a configuration in which the length of the first core shaft part 11A in the axial direction of the core shaft 10A is less than 5 mm, it can be difficult to shape the distal end part. In the present embodiments, the length of the first core shaft part 11A in the axial direction of the core shaft 10A can be 5 mm or more, and thus, it is easy to shape the distal end part. However, the length of the first core shaft part 11A in the axial direction of the core shaft 10A is preferably 15 mm or less, to avoid whipping, as described above.

In the guide wire 100A, the first core shaft part 11A can be formed of a material containing stainless steel. Stainless steel can be plastically deformed more easily than other materials, and thus, the deformation from the shaping tends to be retained without the guide wire 100A returning to its original shape, so that the first core shaft part 11A can be easily shaped.

In the guide wire 100A, the core shaft 10A includes second core shaft part 12, which can be formed of a material containing a superelastic alloy. Thus, for the same reason as in the case of the guide wire 100, the operability and vascular selectivity of the guide wire 100A can be maintained, even when the first core shaft part 11A can be easily bent in the specific plane direction in the shaping as described above.

Figure 16:
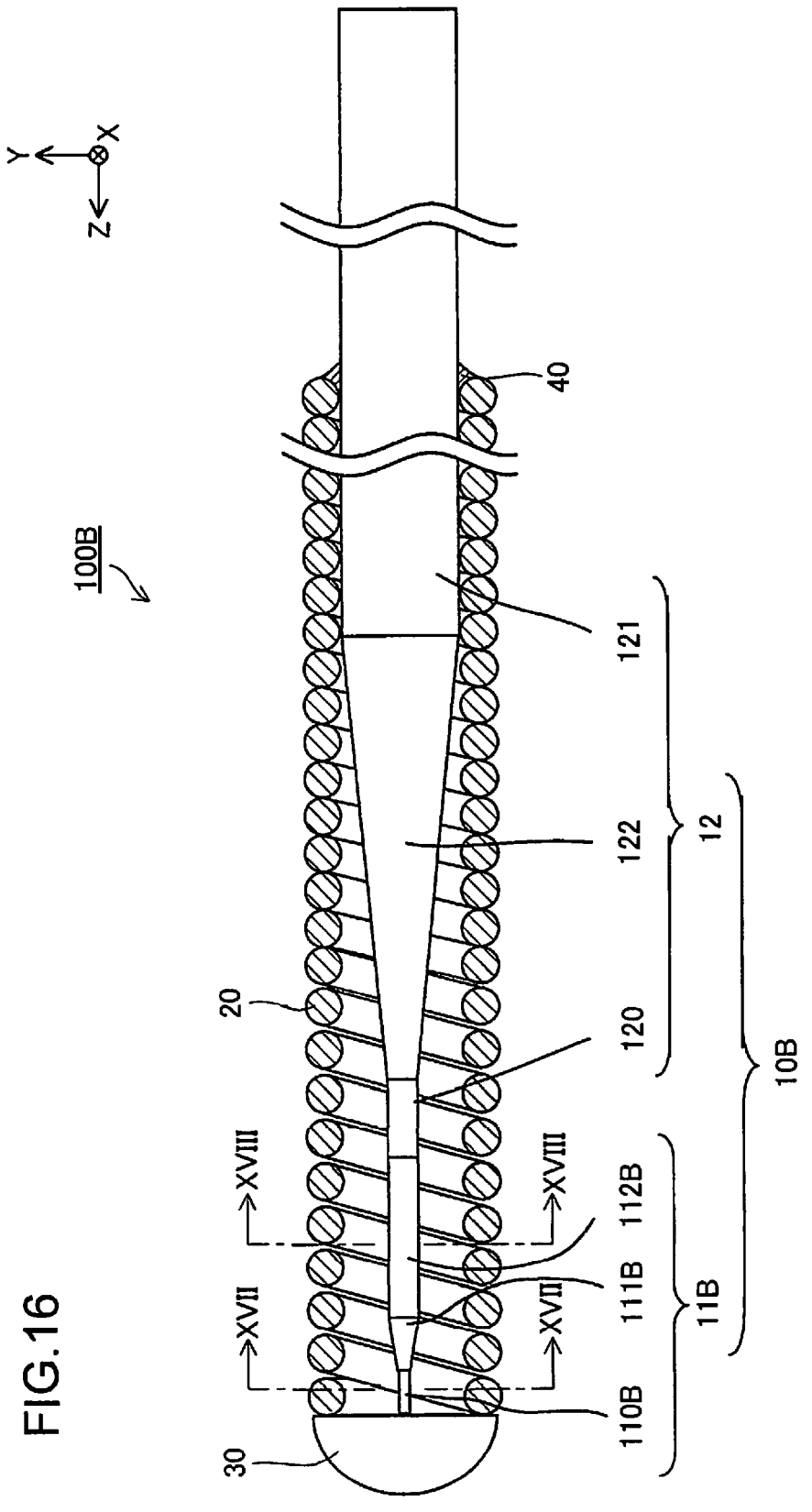
FIG. 16 is a side view of a guide wire in a third embodiment.
Figure 17:
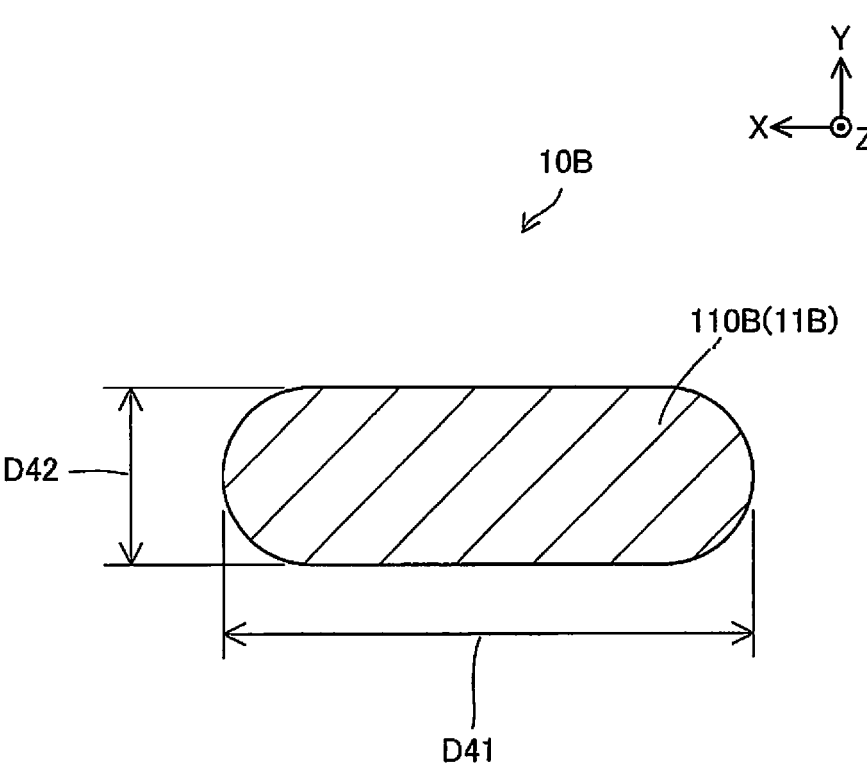
FIG. 17 is a cross-sectional view of the core shaft of the guide wire shown in FIG. 16 taken along line XVII-XVII.
Figure 18:
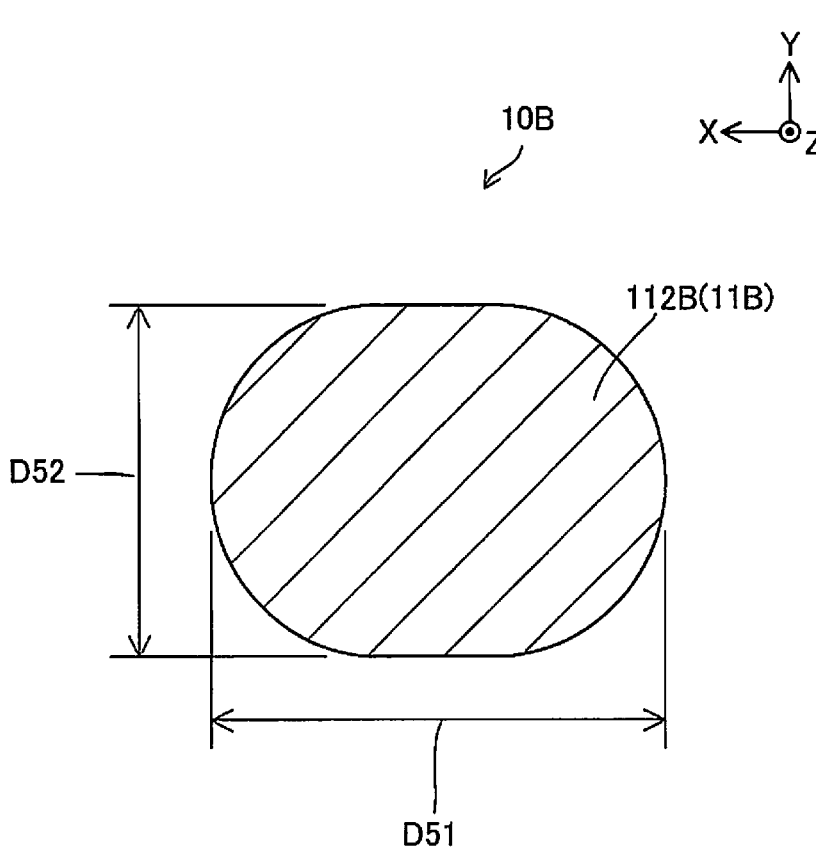
FIG. 18 is a cross-sectional view of the core shaft of the guide wire shown in FIG. 16 taken along line XVIII-XVIII.

FIG. 16 is a side view of a guide wire 100B in a third embodiment. FIG. 17 is a cross-sectional view of a core shaft 10B at a position XVII-XVII of FIG. 16. FIG. 18 is a cross-sectional view of the core shaft 10B at a position XVIII-XVIII of FIG. 16. The guide wire 100B can differ from the guide wire 100, described above, in the configuration of the core shaft 10B. In the following, components of the guide wire 100B that are the same as those of the guide wire 100 will be referred to by the same reference numerals, and description thereof will be omitted where appropriate.

As illustrated in FIG. 16, the core shaft 10B is a rod-shaped member having a diameter that is smaller at the distal end side than at the proximal end side. The core shaft 10B includes a first core shaft part 11B including the distal end of the core shaft 10B and a second core shaft part 12 located proximal to the first core shaft part 11B. In the core shaft 10B, the first core shaft part 11B and the second core shaft part 12 can be integrally formed. The core shaft 10B may be formed of a material containing stainless steel (e.g., SUS302, SUS304, SUS316, or the like).

As illustrated in FIGS. 17 and 18, the first core shaft part 11B includes a strongly oblate part 110B, a tapered portion 111B, and a slightly oblate part 112B, which have transverse cross-sections with a shape similar to the strongly oblate part 110, the tapered portion 111, and the slightly oblate part 112 of the first core shaft part 11 of guide wire 100, respectively.

The guide wire 100B includes the core shaft 10B. The core shaft 10B includes the slightly oblate part 112B (of the first core shaft part 11B), which is located on the distal end side of the core shaft 10B and has an oblateness of between 7% and 35%. The length of the slightly oblate part 112B of the first core shaft part 11B in the axial direction of the core shaft 10B (e.g., Z-axis direction) can be 5 mm or more.

Thus, for the same reason as in the case of the guide wire 100, the rotation performance of the guide wire 100B can be maintained, even when the slightly oblate part 112B of the first core shaft part 11B can be easily bent in the specific plane direction in the shaping.

In the guide wire 100B, the wire diameter of the slightly oblate part 112B of the first core shaft part 11B can be 40 μm or more. In this way and others, the rotation performance of the guide wire 100B can be more better controlled for the same reason as in the case of the guide wire 100.

In the guide wire 100B, a maximum diameter D51 (or wire diameter) of the slightly oblate part 112B of the first core shaft part 11B can be 80 μm or more.

In the guide wire 100B, the slightly oblate part 112B of the first core shaft part 11B may be formed of a material containing stainless steel. Stainless steel can be plastically deformed more easily than other materials, and thus, the deformation from the shaping tends to be retained without the guide wire 100B returning to its original shape, so that the shaping can be easily performed.

In the guide wire 100B, the strongly oblate part 110B, which is located closer to the distal end of the core shaft 10B than the slightly oblate part 112B of the first core shaft part 11B, can have an oblateness of 40% or more. Thus, for the same reason as guide wire 100, the guide wire 100B is suitable to be used in a state where the slightly oblate part 112B of the first core shaft part 11B is bent to have a relatively small curvature and the strongly oblate part 110B is bent to have a relatively large curvature.

In the guide wire 100B, the direction of the maximum diameter D51 of the slightly oblate part 112B of the first core shaft part 11B and the direction of the maximum diameter D51 of the strongly oblate part 110B of the first core shaft part 11B can be parallel to each other. Thus, for the same reason as guide wire 100, the directionality of deformation of the guide wire 100B from the shaping can be limited to the specific plane direction (or a direction close to the specific plane direction).

In the guide wire 100B, the strongly oblate part 110B of the first core shaft part 11B can be formed of a material containing stainless steel and the deformation from the shaping tends to be retained without the guide wire 100B returning to its original shape, so that the guide wire 100B can be easily shaped, as described herein.

Figure 19:
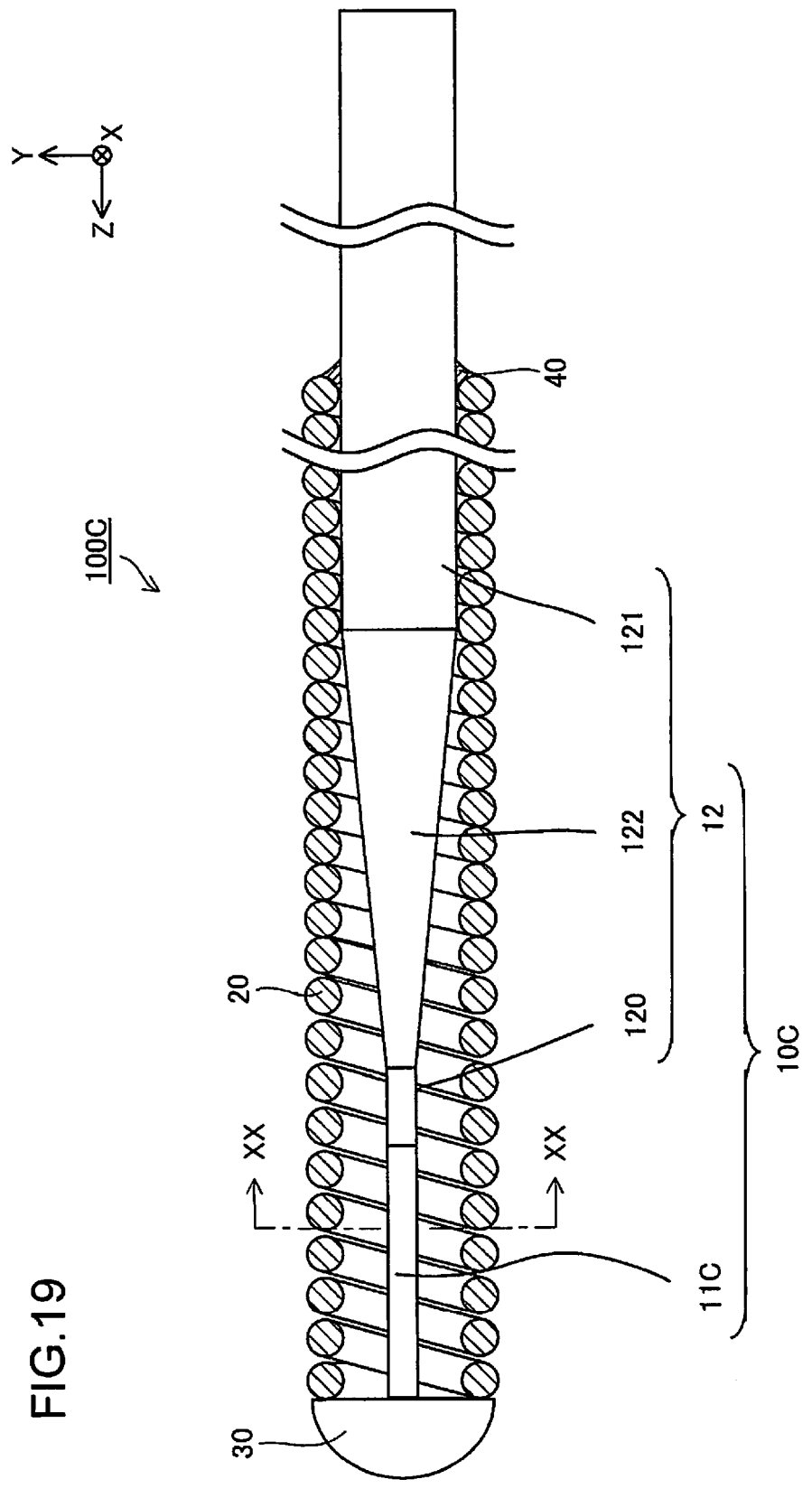
FIG. 19 is a side view of a guide wire in a fourth embodiment.
Figure 20:
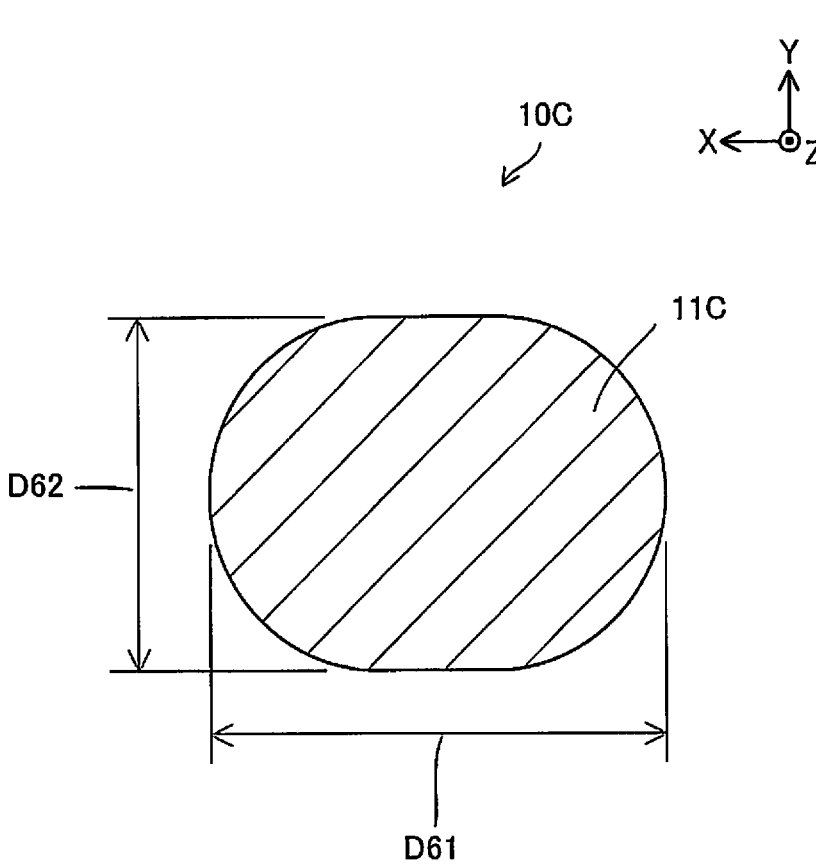
FIG. 20 is a cross-sectional of the core shaft of the guide wire shown in FIG. 19 taken along line XX-XX.

FIG. 19 is a side view of a guide wire 100C in a fourth embodiment. FIG. 20 is a cross-sectional view of a core shaft 10C at a position XX-XX of FIG. 19. The guide wire 100C may differ from the configuration of the guide wires, described above, in the configuration of the core shaft 10C. In the following, components of the guide wire 100C that are the same as those of the guide wire 100A will be referred to by the same reference numerals, and description thereof will be omitted where appropriate.

As illustrated in FIG. 19, the core shaft 10C is a rod-shaped member having a diameter at the distal end side that is smaller than a diameter at the proximal end side. The core shaft 10C includes a first core shaft part 11C including the distal end of the core shaft 10C and a second core shaft part 12 located proximal to the first core shaft part 11C. In the core shaft 10C, the first core shaft part 11C and the second core shaft part 12 may be integrally formed. The core shaft 10C can be formed of a material containing stainless steel (e.g., SUS302, SUS304, SUS316, or the like).

As illustrated in FIG. 20, the first core shaft part 11C has a transverse cross-section having a shape similar to the first core shaft part 11A.

The guide wire 100C includes the core shaft 10C. The core shaft 10C includes the first core shaft part 11C, which is located on the distal end side of the core shaft 10C, and can have an oblateness between 7% and 35%. The length of the first core shaft part 11C in the axial direction of the core shaft 10C (e.g., Z-axis direction) can be 5 mm or more.

In the guide wire 100C, the oblateness of the first core shaft part 11C can be between 7% and 35%, as described above. Thus, as described herein, the rotation performance of the guide wire 100C can be maintained, even when the first core shaft part 11C can be easily bent in the specific plane direction in the shaping.

In the guide wire 100C, the first core shaft part 11C may be formed of a material containing stainless steel and the deformation from the shaping tends to be retained without the guide wire 100C returning to its original shape, so that the guide wire 100C can be easily shaped, as described herein.

The techniques disclosed herein are not limited to the above-described embodiments, and may be modified into various modes without departing from the spirit of the above-described embodiments. For example, the following modifications can be applied.

The configurations of the guide wires 100 and 100A in the embodiments described above are merely examples and various modifications can be applied.

For example, the first embodiment described above may have a configuration in which the direction of the maximum diameter D21 of the slightly oblate part 112 of the first core shaft part 11 and the direction of the maximum diameter D11 of the strongly oblate part 110 of the first core shaft part 11 are not parallel to each other.

In the embodiments described above, the distal end-side joint part 30 may not be provided in the guide wires 100, 100A, 100B, and 100C.

Further, the materials of the members constituting the guide wires 100, 100A, 100B, and 100C of the embodiments described above are merely examples and various modifications are possible. These examples are not inclusive and a skilled person would understand that other modifications can be made without departing from the scope of the described embodiments.

What is claimed is:

1. A guide wire comprising:

a core shaft having a maximum diameter in a cross section orthogonal to an axial direction of the core shaft and an orthogonal diameter in a direction orthogonal to a direction of the maximum diameter in the cross section, the core shaft including a first specific portion located on a distal portion of the core shaft and having an oblateness of between 7% and 35%, wherein:

the first specific portion extends 5 mm or more in the axial direction;

oblateness is equal to a difference between the maximum diameter and the orthogonal diameter divided by the maximum diameter;

the core shaft further includes a tapered portion adjacent to a tip of the first specific portion, the tapered portion having a gradually-changing oblateness;

the core shaft includes a second specific portion located closer to a distal end of the core shaft than the first specific portion, the second specific portion having the oblateness of 40% or more and a length; and the first specific portion having a length that is longer than the length of the second specific portion.

2. The guide wire according to claim 1, wherein the first specific portion is formed of a material containing stainless steel.

3. The guide wire according to claim 1, wherein a direction of the maximum diameter of the first specific portion and a direction of the maximum diameter of the second specific portion are parallel to each other.

4. The guide wire according to claim 1, wherein the second specific portion is formed of a material containing stainless steel.

5. The guide wire according to claim 1, wherein the core shaft includes a superelastic portion located closer to a proximal end of the guide wire than the first specific portion; and the superelastic portion includes a superelastic alloy.

6. The guide wire according to claim 1, wherein the second specific portion is adjacent to a tip of the tapered portion.

* * * * *